United States Patent
Wicks et al.

(10) Patent No.: US 6,262,405 B1
(45) Date of Patent: *Jul. 17, 2001

(54) MEDICAL WASTE TREATMENT AND DECONTAMINATION SYSTEM

(75) Inventors: George G. Wicks; Rebecca L. Schulz, both of Aiken, SC (US); David E. Clark, Gainesville, FL (US)

(73) Assignee: Westinghouse Savannah River Company, Aiken, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/382,758

(22) Filed: Aug. 25, 1999

Related U.S. Application Data

(63) Continuation-in-part of application No. 08/911,411, filed on Aug. 14, 1997, now Pat. No. 5,968,400.

(51) Int. Cl.⁷ ...................................................... H05B 6/80
(52) U.S. Cl. ........................ 219/679; 219/680; 219/759; 422/21
(58) Field of Search .................................... 219/679, 678, 219/680, 681, 682, 686, 757, 759, 756, 701; 422/21

(56) References Cited

U.S. PATENT DOCUMENTS

| 4,940,865 | * 7/1990 | Johnson et al. ...................... 219/753 |
|---|---|---|
| 5,035,858 | 7/1991 | Held et al. . |
| 5,166,488 | * 11/1992 | Peppard ................................ 219/759 |
| 5,213,758 | 5/1993 | Kawashima et al. . |
| 5,270,000 | 12/1993 | Goldner et al. . |
| 5,277,868 | 1/1994 | Langford . |
| 5,322,603 | 6/1994 | Kameda et al. . |
| 5,348,235 | 9/1994 | Pappas . |
| 5,429,799 | 7/1995 | Sheih et al. . |
| 5,441,622 | 8/1995 | Langford . |
| 5,540,886 | 7/1996 | Warmbier et al. . |
| 5,968,400 | * 10/1999 | Wicks et al. ......................... 219/679 |

* cited by examiner

Primary Examiner—Philip H. Leung
(74) Attorney, Agent, or Firm—Dority & Manning, PA

(57) ABSTRACT

The invention discloses a tandem microwave system consisting of a primary chamber in which hybrid microwave energy is used for the controlled combustion of materials. A second chamber is used to further treat the off-gases from the primary chamber by passage through a susceptor matrix subjected to additional hybrid microwave energy. The direct microwave radiation and elevated temperatures provide for significant reductions in the qualitative and quantitative emissions of the treated off gases. The tandem microwave system can be utilized for disinfecting wastes, sterilizing materials, and/or modifying the form of wastes to solidify organic or inorganic materials. The simple design allows on-site treatment of waste by small volume waste generators.

15 Claims, 2 Drawing Sheets

MEDICAL WASTE TREATMENT AND DECONTAMINATION SYSTEM

RELATED APPLICATIONS

This application is a continuation-in-part of application serial number 08/911,411 filed Aug. 14, 1997, and which issued on Oct. 19, 1999, as U.S. Pat. No. 5,968,400 entitled "TANDEM MICROWAVE WASTE REMEDIATION AND DECONTAMINATION SYSTEM" and which is incorporated herein by reference.

STATEMENT AS TO RIGHTS TO INVENTIONS MADE UNDER FEDERALLY SPONSORED RESEARCH AND DEVELOPMENT

The U.S. Government has rights in this invention pursuant to Contract No. DE-AC09-89SR18035 and Contract No. DE-AC09-96SR18500 between Westinghouse Savannah River Company and the U.S. Department of Energy.

BACKGROUND OF THE INVENTION

1. Field of the Invention

This invention relates to use of microwave energy to treat medical waste materials. Medical waste comprises a diverse mixture of materials which may include metal, glass, plastic, paper, various other organic materials. Further, many of these materials have been exposed to bacterial or viral pathogens.

Medical waste disposal presents multiple concerns. Foremost, medical waste represents a biological hazard. Accordingly, typically, medical waste must be sterilized through heat or chemical methods prior to its subsequent handling and disposal. Secondly, many components of the medical waste stream remain hazardous following sterilization. For instance, "sharps", such as syringe needles, scalpel blades, razors, glass pipettes, lances, and similar items remain a physical risk to waste handlers and create additional problems in waste packaging. Sharp objects within the waste can readily puncture bags or other containers used to segregate the waste.

Further, the sheer volume of medical waste contributes to the high cost of disposal. In recent years, there has been an increased reliance upon disposable, pre-sterilized instrumentation and supplies. As a result, there is a great deal of waste generated including plastic vials and containers, disposable surgical gowns and drapes, used dressings and gauze material, and similar high bulk waste materials. Such materials add greatly to the waste stream and the resulting disposal cost of medical waste.

Yet an additional problem relates to the large number of waste generating sites. Each doctor's office, clinic, veterinary facility, hospital, and other health care facility where patients are seen and treated generate medical waste. Heretofore, it has not been possible to effectively treat the waste at each location where generated. As a result, the waste has to be properly packaged, sterilized, and shipped to a subsequent disposal facility.

Finally, the traditional methods of handling medical waste have done very little to alter the form, structure, and physical identity of the waste. Recognizable medical waste is an obstacle to introducing medical waste into the normal sanitation waste stream. As a result, there is a need to alter the physical state of the medical waste so as to produce an unrecognizable, yet harmless waste product. Accordingly, there remains much room for improvement and variation within the art.

2. Description of Related Art

It is known in the art to use microwaves to sterilize and to further treat medical waste. U.S. Pat. No. 5,166,488 to Peppard, incorporated herein by reference, teaches an apparatus which uses microwaves to melt hypodermic syringes. U.S. Pat. No. 4,940,865 provides an apparatus for melting materials using microwaves. However, the efficiency of these microwave treatments are questionable in that these techniques result in the generation of gaseous and airborne particulates which require costly filtering and containment systems. As such, these systems are not suitable for small volume waste generators such as an individual medical office or clinic. Accordingly, there remains room for improvement within the art of microwave processing of waste.

SUMMARY OF THE INVENTION

It is an object of this invention to provide an apparatus and process which uses microwave radiation to physically transform a diverse waste material into an unrecognizable end product.

It is a further object of this invention to provide an apparatus and a process to treat off-gas emissions from the microwave destruction of medical waste such that the treated emissions may be discharged into the atmosphere.

It is a further and more particular object of this invention to provide a two-stage microwave treatment apparatus and process wherein a first microwave chamber is used to treat a solid or liquid waste material and a second microwave waste chamber is used to treat the generated off-gases from the first chamber.

It is a further and more particular object of this invention to provide a medical waste disposal apparatus and process which uses hybrid microwave heating and improves the efficiency of the process for treatment of a wide range of materials.

It is still a further and more particular object of this invention to provide an apparatus and process for simultaneously treating a mixture of paper, plastic, liquids, glass, and metal containing waste, wherein the volume and physical shape of the waste is transformed into an unrecognizable solid end product (example, ash) and the resulting off-gas emissions are further treated with additional microwave radiation, transforming the off-gas emissions into a gaseous end product which may be safely released into the atmosphere.

It is also a feature of the proposed technology to allow: a) disinfection; b) sterilization; and c) destruction of medical wastes, dependent on customer needs.

These and other objects of the invention are accomplished by an apparatus and process that provides for a tandem hybrid microwave waste disposal system comprising:

a first combustion chamber for housing medical waste and in communication with a source of microwaves;

a second combustion chamber in communication with a second source of microwaves, the second combustion chamber having an input region in communication with a first end of a conduit, a second end of the conduit in communication with the first combustion chamber, the second combustion chamber further defining a susceptor defining a gas permeable matrix;

an exhaust port in communication with an output region of the second combustion chamber, wherein evolved combustion off-gases from the first combustion chamber pass through the conduit into an input region of the second combustion chamber whereby the susceptor matrix and other possible constituents, such as ion-exchange type materials, are maintained at an effective temperature for treating the off-gases, the treated off-gases exiting through an exhaust port.

Such an apparatus enables the process of treating medical waste comprising:

providing a supply of medical waste material within a combustion chamber, passing a fluid stream through the combustion chamber;

exposing the medical waste material to a combination of microwave energy and radiant energy, the radiant energy supplied by a susceptor in proximity to the medical waste material;

directing off-gases from the first combustion chamber to a second combustion chamber;

radiating the off-gases in the combustion chamber with microwave energy;

retaining the off-gases within the second combustion chamber until an effective amount of off-gases are destroyed, thereby providing treated off-gases; and venting the treated off-gases.

The invention is an improvement over prior methods of using microwave energy to treat medical waste. The present invention provides a sterilization process, a physical transformation process, and a subsequent off-gas treatment process such that the medical waste, following treatment, has been rendered to a releasable off-gas and a charred mixture of powder, and/or melted glass, and melted metal. The off-gases associated with the microwave treatment are combusted to innocuous end products in association with high temperature environments produced by microwave energy in combination with selected susceptor material. The resulting treated medical waste is a decontaminated and sterilized material which may be disposed of in a normal sanitation waste stream.

DETAILED DESCRIPTION OF THE INVENTION

As used herein, the term "medical waste" includes a diverse mixture of materials. The present invention is applicable for treatment of materials having organic tissue/fluids of human or animal origin including fecal matter, body parts and organs, blood, urine, hair, bone, pathology samples, and biopsy materials. Instrumentation suitable for disposal with the microwave apparatus and process includes needles, syringes, probes and sensors, retractors, lancets, tongue depressors, scalpels, cotton swabs, and related assisting apparatus and materials. Various types of plastics may be included in medical waste including tubing and valves, IV tubing, IV bags, drainage tubes, packaging bags, latex gloves, non-latex gloves, splash goggles/masks, packaging materials and containers, instrument protective coverings, and thermometer coverings.

The term "medical waste" also includes a variety of fabric and materials which would include woven materials, bedding, towels, drape materials, bandages, masks, filters, gauze, adhesive tape, elastic bandages, toilet/facial tissue, absorbent padding, hospital-provided clothing, patient's personal contaminated clothing, feminine protection products, diapers, diagnostic equipment, slides, caps, gowns, boots, filters, and antiseptic wipes. It should be noted that the instrumentation referenced above will often have a plurality of different materials including plastics, metal and glass.

Metal materials often found within medical waste include metal syringes, bullets, pins, plates, and staples. A diverse range of chemicals would also be present in the waste and would include an enormous variety of drugs and pharmaceutical products, aromatic and alaphetic hydrocarbons including xylene, paints, paint thinner, and hydraulic fluid. Further, diverse and complex chemicals would be present in processing solutions and sterilizing solutions associated with medical waste. Further, the medical waste treatment apparatus and process are compatible with miscellaneous materials often found within medical waste streams including plaster, supporting fiberglass additives, suture materials, various forms of glass, dentistry materials including teeth, filling material, dentures, molds, as well as food waste including grease, paper products, x-ray materials and film.

Figure 1:
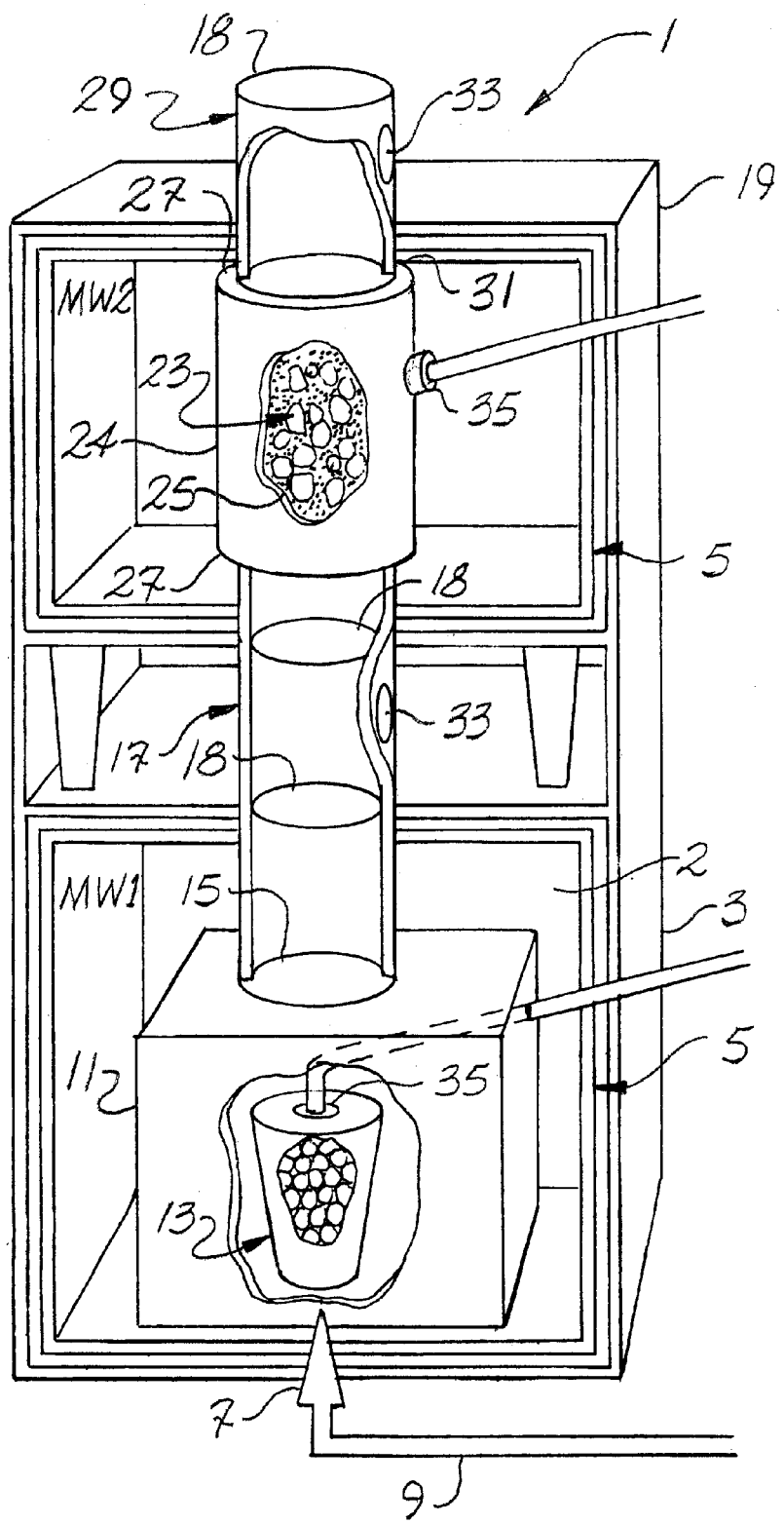
FIG. 1 depicts a schematic of a tandem microwave waste processing apparatus in accordance with this invention.

As seen in reference to FIG. 1, a preferred embodiment of a tandem microwave medical waste treatment apparatus 1 is illustrated. A first primary chamber 2 is defined by the interior of a conventional household 900 watt, 2.45 Ghz microwave unit 3 which has been lined along interior surfaces with a refractory lining 5. An air inlet 7 has been provided along a bottom surface of the microwave unit 3. Inlet 7 is in communication through feed line 9 with a supply of compressed gas. Preferably, the compressed gas is an inert gas, such as argon or nitrogen, and can be introduced to the primary chamber at a controlled rate. The use of inert gases is useful to control the combustion rate and to avoid explosive operating conditions. However, it has been demonstrated that for some medical waste materials, a simple air stream will suffice. In general, the less organic material present in the primary combustion chamber 2, the less need there is for an inert gas stream. Alternatively, a partial vacuum may be established within the chamber 2 which will also control the combustion rate.

In the illustrated preferred embodiment, a walled, covered box-like enclosure 11 of susceptor material such as SiC is placed over crucible 13 within chamber 2 of the combustion chamber. The crucible 13 is used to hold the medical waste material which is to be processed. An upper surface of the susceptor enclosure 11 defined in opening 15 is in communication with a tube 17.

As seen in FIG. 1, tube 17 is in communication with an interior of a second conventional microwave unit 19, positioned a spaced distance above unit 3. While the illustrated embodiment sets forth the preferred positioning of the off-gas unit 3, the relative positioning and distance of the units may be varied and could include side-by-side configurations or substantial special separations through the use of an intervening conduit connector.

Similar to unit 3, a refractory lining 5 surrounds an interior 21 of microwave unit 19. A terminal end of tube 17 is interconnected to a combustion chamber 23. Optional filters 18 may be provided within tube 17 to control particulate emissions. Combustion chamber 23 is provided by a mullite or alundum (St. Gobain/Norton Industrial Ceramics Corp.) passageway, such as a tube 24, partially filled within its interior with a SiC bed of 16 grit size material as indicated with reference numeral 25. Alternatively, chamber 23 can be filled with a plurality of stacked, reticulated SiC filters as well as other appropriate susceptor materials (such as refractory materials used to make fire bricks) and mixtures thereof. Chamber 23 and material 25 provide operating temperatures of the susceptor material of between 1,000 to 1,200° C. Reticulated phosphate bonded alumina (PBA) filters 27 may be placed at either end of chamber 23 to maintain the stability of the bed and to increase the gas emission residence time in the chamber. Design features, such as a serpentine pathway or tube, can also be used to increase residence time. Further, the passageway which defines chamber 23 may be of any shape or configuration which permits the passage therethrough of the combustion gas.

An exhaust port 29 exits microwave unit 19 and is in communication at a first end with a terminal 31 of chamber 23. Sampling ports 33 are provided on both exhaust port 29 and exhaust tube 17 to facilitate collection of gas stream samples for analysis. Thermocouples 35 may be provided on both the combustion chamber 23 as well as crucible 13 to provide displayed operating temperature conditions.

In operation, medical waste material is placed within crucible 13 of microwave unit 3. Microwave unit 19 is operated to bring the SiC susceptor material 25 within chamber 23 to an operating temperature of between about 1,000–1,200° C. Once the operating temperature conditions are obtained, the microwave unit 3 is used to treat the material inside crucible 13 with a combination of direct microwave energy as well as indirect infrared energy which radiates from the susceptor. The microwave energy input of both units 19 and 3 can be easily controlled to achieve a desired combustion rate of the solid material as well as effective operating temperature for the treatment of off-gases within chamber 23.

Figure 2:
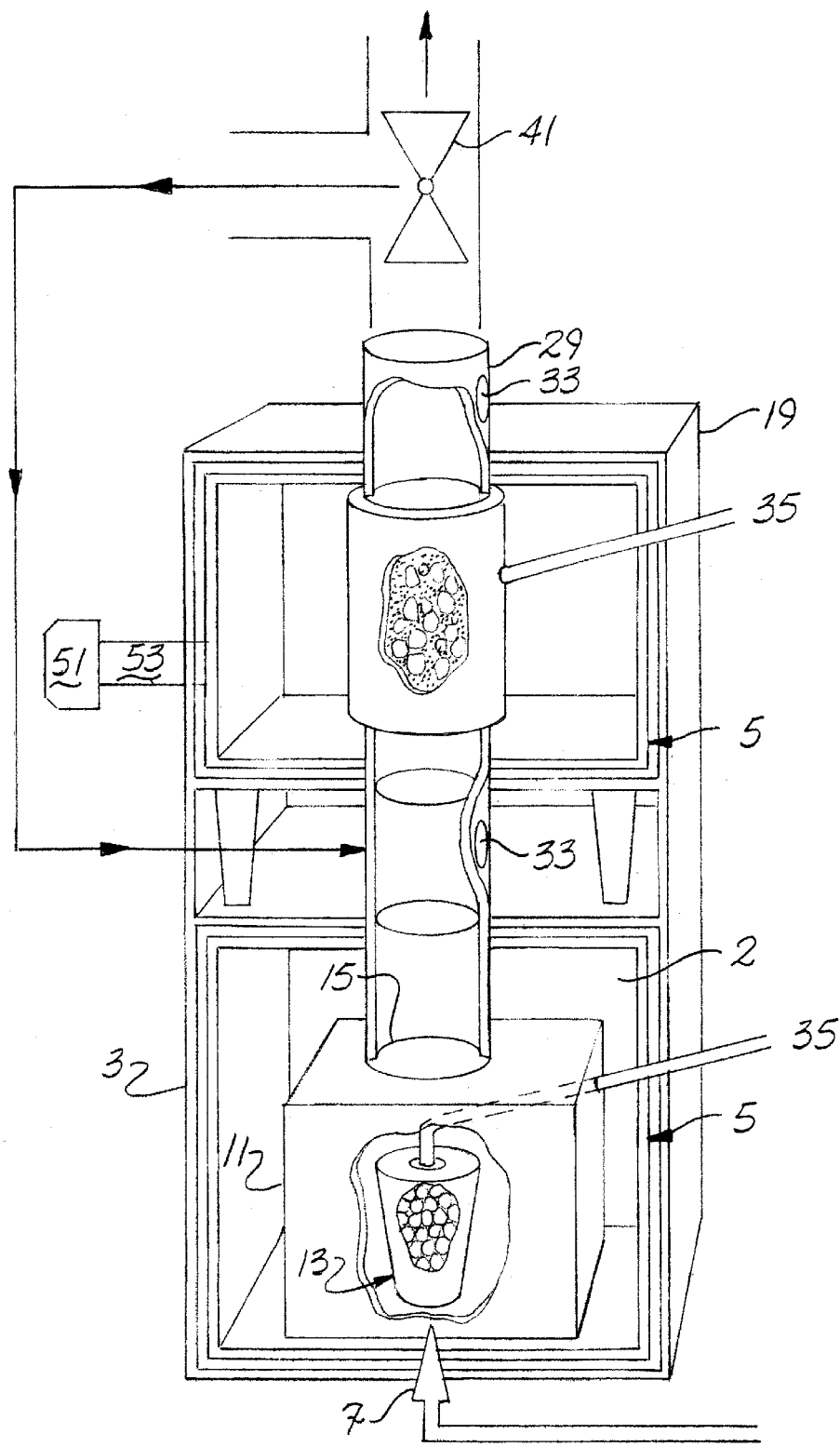
FIG. 2 depicts an alternative schematic configuration of the microwave waste processing apparatus of this invention.

The process can be further controlled by the use of inert gases to provide a regulated fluid flow through the system. The sampling ports 33 provide the operator the ability to sample the off-gas streams following both the material waste treatment and the off-gas treatment. The data from the following examples may be collected by using Tenax-TA filled glass air traps (OI Analytical, College Station, Texas) which are highly absorbent for C6–C20 compounds. Following collection, the air traps can be submitted for gas chromatography and mass spectrometry (GC-MS) analysis of the retained off-gases. It is envisioned that sampling ports 33 may be equipped with in-line monitors to provide real-time data collection with respect to off-gas constituents. As seen in FIG. 2, a valve 41 can be used to control the venting of treated off-gases. Should on-line monitors detect unacceptable levels of materials in the off-gas stream, the off-gas pathway can be diverted for retreatment (see directional arrows) to the off-gas combustion chamber.

A continuous batch-type apparatus and process may also be provided by using a conveyor-type system to introduce medical waste into the lower combustion chamber of microwave unit 3. The continuous feed conveyor transports the medical waste to a location where a mixture of direct microwave heating and infrared heating from the susceptor material is used to treat the medical waste.

One difficulty in the combustion of medical waste materials involves the ability to rapidly achieve sufficiently high temperature to sterilize and physically transform the medical waste. As evidenced by the diverse materials which comprise medical waste, equally diverse combustion off-gases will be generated by the initial microwave treatment and process. As set forth in applicant's co-pending application having Serial No. 09/911,411, the dual microwave system has demonstrated its effectiveness with respect to non-medical waste having plastics, glass and metal components. Further, applicant's co-pending application demonstrated the effectiveness of treating numerous gaseous organic chemicals, rendering the treated off-gas to non-detectable concentrations and/or reductions of one order of magnitude.

Preferred embodiments of the apparatus were used to evaluate the apparatus and resulting process with reference to several different types of mixed waste. Further, medical waste was specifically evaluated and the treatment conditions are set forth in the following examples.

EXAMPLE 1

Set forth in tables 1 and 2 are the conditions and results of seven 30 minute test runs (SR-1 through SR-7) using crushed and pulverized printed electrical circuit boards as the waste material. Circuit board material was initial selected as a test material since circuit boards have a mixture of organics and metal. The material is also dense and the organic material will produce a high volume of diverse off-gases which will require treatment. The data was collected using a side-by-side microwave unit configuration as disclosed and discussed in Schulz, R.L., Folz, D.C., Clark, D.E., Schmidt, C.J. and Wicks, G.G., "Microwave Treatment of Emissions from Waste Materials", Microwave Processing of Materials V, M.F. Iskander, J.o. Kiggans, Jr., C. Bolomey, eds., Materials Research Society Symposium Proceedings, Vol. 430, pp. 549–554 (1996).

The gaseous organic compounds that vaporize during treatment of the material in the primary chamber, were sampled at the gas sampling port 33 at the exit of the primary chamber. These values are provided in column A in Table 2. The gases were sampled following treatment in the off-gas combustion chamber and the values reported in column B of Table 2. The results demonstrate reduction of certain organic chemical off-gas concentrations to non-detectable (ND) concentrations, and reductions of other organic chemical off-gas concentrations to more than 1 order of magnitude.

TABLE 1

| Sample ID | Initial Weight (g) | Final Weight | % Wt Loss | Processing/ Off-gas Collection Time (min) | Duty Cycle* (%) |
|---|---|---|---|---|---|
| SR1 | 69.96 | 41.15 | 41.2 | 30 | 50 |
| SR2 | 70.09 | 40.66 | 41.9 | 30 | 50 |
| SR3 | 69.99 | 45.75 | 34.6 | 30 | 50 |
| SR4 | 70.05 | 41.16 | 41.2 | 30 | 100 |
| SR5 | 70.01 | 42.27 | 39.6 | 30 | 50 |
| SR6 | 70.00 | 40.85 | 41.6 | 30 | 50 |
| SR7 | 70.03 | 44.49 | 36.4 | 30 | 50 |

*Percent of time interval magnetron was activated

TABLE 2

A Summary of the GC mass Spectroscopy Results of Emissions Resulting from Combustion of Printed Circuit Boards.
(A = before microwave off-gas treatment; B = after microwave off-gas treatment).

| Compound | SR-1 (ppb) | | SR-2 (ppb) | | SR-3 (ppb) | | SR-4 (ppb) | | SR-5 (ppb) | | SR-6 (ppb) | | SR-7 (ppb) | |
|---|---|---|---|---|---|---|---|---|---|---|---|---|---|---|
| | A | B | A | B | A | B | A | B | A | B | A | B | A | B |
| Benzene* | 16.9 | 1.1 | 14.2 | nd | 19.8 | nd | 115.3 | 5.2 | 119.6 | 8.1 | 176.6 | 14.7 | 165.4 | 13.5 |
| Toluene | 28.7 | 2.7 | 24.4 | nd | 32.6 | nd | 67.5 | 6.1 | 78.7 | 6.9 | 159.1 | 18.1 | 115.7 | 5.9 |
| Ethylbenzene* | 18.7 | nd** | 19.0 | nd | 7.8 | nd | 13.9 | nd | 26.7 | nd | 142.9 | 5.0 | 91.8 | nd |
| Styrene* | 38.7 | 1.2 | 66.6 | nd | 15.0 | nd | 165.2 | 2.9 | 167.7 | 2.6 | 472.3 | 27.2 | 482.9 | 6.5 |
| Napthalane* | 1.2 | nd | 11.0 | nd | nd | nd | 75.1 | 1.3 | 35.2 | 1.3 | 6.8 | 3.4 | 47.6 | 2.4 |
| m/p Xylene* | 17.5 | nd | 1.9 | nd | nd | nd | 27.5 | nd | 23.8 | nd | 53.3 | 1.6 | 60.0 | nd |
| 1,3,5 Trimethylbenzene | 9.5 | nd | 12.4 | nd | 1.3 | nd | 15.6 | 1.6 | 18.4 | nd | 12.8 | 2.4 | 46.2 | 1.7 |
| 1,2,4 Trimethylbenzene | 17.5 | nd | 1.7 | nd | nd | nd | nd | nd | nd | nd | 15.1 | nd | 6.1 | 1.8 |

*Listed in the Clean Air Act (as amended, 1990) as hazardous air pollutants [14].
**nd = not detected (<1 ppb)

EXAMPLE 2

Set forth in Table 3 below is data from two additional runs using crushed and pulverized circuit boards and following the general protocol set forth above in an upper/lower tandem microwave system as seen in FIG. 1. As set forth in Table 3, the results of the emissions analysis is set forth in nanograms. Again, significant reductions and/or elimination of certain emission waste has been obtained.

Table 3. Gas Chromatography Data Collected Before and After Microwave Treatment of Emissions Resulting From the Combustion of Unreinforced Circuit Boards

TABLE 3

Gas Chromatography Data Collected Before
and After Microwave Treatment of Emissions Resulting
From the Combustion of Unreinforced Circuit Boards

| COMPOUND | SR-8 EMISSIONS (ng) | | SR-9 EMISSIONS (ng) | |
|---|---|---|---|---|
| | A | B | A | B |
| Benzene* | 5838.9 | 22.2 | 1415.6 | 139.5 |
| Toluene* | 8146.6 | 15.7 | 4215.9 | 158.7 |
| Ethylbenzene* | 1147.4 | nd | 4557.0 | 5.2 |
| Styrene* | 1666.9 | 6.2 | 20012.0 | 38.4 |
| Naphthalene* | 355.5 | nd | 2403.6 | 27.9 |
| m/p Xylene* | 2259.0 | nd | 510.6 | nd |
| 1,3,5 Trimethylbenzene | 1564.0 | nd | 378.7 | 64.3 |
| 1,2,4 Trimethylbenzene | 904.7 | nd | 171.8 | nd |

A = before microwave off-gas treatment; B = after microwave off-gas treatment
*Listed in the Clean Air Act (as amended, 1990) as hazardous air pollutants.

The reductions in off-gas constituents are significant and have applications for a variety of off-gas emission sources, regardless of origin. Further, the data is from a combustion treatment chamber having a simple cylindrical shape and a length of approximately 8 inches. By varying the geometry and length of the treatment chamber, is should be possible to increase the volume of introduced off-gases along with enhanced efficiency of the treatment process.

EXAMPLE 3

Medical waste in the form of a surgical right side disposable legging was treated in the apparatus seen in reference to FIG. 1. The surgical legging evaluated is a Kimberly-Clark Corporation product and comprises a fabric having several fabric layers including meltable polymer layers. The legging was placed within crucible 13. A variety of process times and maximum processing temperatures were selected to evaluate different treatment conditions.

During the processing of the medical waste, separate off-gas data was not obtained. However, the data set forth in Examples 1 and 2 above, with electronic circuitry which includes diverse plastics, papers, and metals, verified that diverse, toxic emissions may be destroyed and decomposed to dischargeable levels. Given the similar nature of the organic materials and based upon applicants' observations during the testing, the off-gas generated by the medical waste is effectively treated by the off-gas treatment portion associated with microwave unit 19.

The treatment conditions and times are set forth in Table 4 and indicate that the medical waste material can be processed to a fine ash residue, reducing the initial 16.95 gram weight of the medical waste to a final solid weight of 0.29 grams.

TABLE 4

| | Process Time (min.) | Max Temp (° C.) | Initial Wt. (g) | Final Wt. (g) | Observations |
|---|---|---|---|---|---|
| Sample 1 | 30 | 175 | 21.67 | 21.36 | 1 |
| Sample 2 | 10 | 311 | 19.23 | 18.38 | 2 |
| Sample 3 | 30 | 555 | 16.95 | 0.29 | 3 |

[1]Partially reduced paper/polymeric material to vitreous mass
[2]Reduced paper/polymeric material to solid vitreous mass
[3]Reduced paper/polymeric material to fine ash residue

EXAMPLE 4

Ribbed plastic tubing and plastic connectors were processed at the conditions and achieving the results as indicated in Table 5. As in Example 3, the off-gas treatment was in operation; however, separate measurements and evaluations were not recorded for the resulting off-gas.

TABLE 5

| Process Time (min.) | Max Temp (° C.) | Initial Wt. (g) | Final Wt. (g) | Observations |
|---|---|---|---|---|
| 20 | 277 | 15.27 | 14.95 | 1 |

[1]charred melted mass - further processing would reduce material to ash

EXAMPLE 5

The apparatus and process was also evaluated with regard to Kimberly-Clark 18 gauge precision glide needle (Model No. 305196) as part of a sharps evaluation. The process conditions and results are set forth in Table 6.

TABLE 6

| Process Time (min.) | Max Temp (° C.) | Initial Wt. (g) | Final Wt. (g) | Observations |
|---|---|---|---|---|
| 120 | >1200° C. | 2.624 | 0.593 | 1 |

[1]Needles did not melt, but did oxidize extensively, easily broken up with minimal pressure (i.e., broke apart with fingers)

EXAMPLE 6

Mixed medical waste was evaluated using the materials as set forth in Table 7 and the process conditions and results as set forth in Table 8.

TABLE 7

| Materials | Sample 1 Weight | Sample 2 Weight |
|---|---|---|
| Back table cover | 10.89g | 9.57g |
| Sterile latex gloves | 19.52g | 12.88g |
| Syringe | 4.29g | 5.32g |
| Plastic vial/H$_2$O | 8.01g | 6.98g |
| Paper/poly drape | 1.48g | 1.30g |
| Sterile gauze pads | 2.57g | 2.53g |
| White paper/poly drape | 6.94g | 9.74g |

TABLE 8

| | Process Time (min.) | Max Temp (° C.) | Initial Wt. (g) | Final Wt. (g) | Observations |
|---|---|---|---|---|---|
| Sample 1 | 75 | 439° C. | 53.69 | 22.39 | 1 |
| Sample 2 | 85 | 601° C. | 47.82 | 4.13 | 2 |

[1]charred black mass, wt. reduction ~60%, some items still somewhat recognizable
[2]charred black mass, wt. reduction >90%

As the above results indicate, it is possible to transform diverse medical waste into a largely unrecognizable charred product. To the limited extent certain medical components such as syringe needles are recognizable, the components are friable and can be rendered unrecognizable with light mechanical pressure. In each instance, it was possible to provide time and temperature treatment conditions which achieved a significant reduction in material weight. Along with the weight reduction, even greater improvements in waste volume were noted as bulky items such as tubing, vials, and other containers were melted and oxidized into a more compact form.

The treatment temperatures and times used are well above the conditions needed to sterilize the materials. One having ordinary skill in the art would recognize that any combination of treatment temperature and time which would render the medical waste into a molten, charred, and substantially unrecognizable form would sterilize any pathogens present within the medical waste.

By way of the data and tables set forth above, it has been well established that the off-gas constituents of waste containing a mixture of organic materials, metals, and glass can be controlled and significantly reduced by the off-gas microwave treatment.

One desirable aspect of the present invention is that the apparatus and process may be operated at each medical waste generator facility. For instance, the use of a standard retail microwave unit requires little space, is compatible with existing electrical supply needs, and the operation of which is well known and easily learned.

In preferred embodiments of the present invention, it is desirable to have operating safeguards in place. One such safeguard is the use of a thermocouple or thermostat to monitor the temperature of the off-gas unit. The primary microwave unit can be designed to be inoperative until a sensor or switch is activated in response to an adequate combustion temperature within the off-gas unit. When controlled in this manner, the generation of off-gases from the microwave treatment process does not occur until the off-gas treatment unit is operative.

The present invention makes use of both direct microwave energy bombardment of the waste material along with radiant infrared heating which occurs through the use of susceptor materials. It is also possible to tune or vary the frequency of the microwave source so as to selectively target certain types or categories of waste constituents. Such targeting is possible in both the primary waste step as well as in the treatment of off-gas emissions.

For instance, it is possible to use separate magnetrons at separate frequencies to sequentially treat off-gases with varying frequencies. For large capacity industrial uses, it is believed preferred that microwaves be generated from one or more remote magnetrons 51 (FIG. 2) and transmitted via waveguides 53. This arrangement shields the magnetron from reflecting microwaves. It also permits innovative designs for combustion chambers to be constructed and may be useful in the design of large volume commercial units. The location of a remote magnetron is particularly useful in developing customized designs for controlling off-gas emissions.

As set forth in the data above, the present invention provides a process which significantly reduces the waste volume and weight of the waste material. Further, the process takes the diverse medical waste and provides a treatment process which renders the waste largely unrecognizable. Where needed, additional mechanical crushing can be used to completely render the product into a harmless, unrecognizable residue which is safe to introduce into a municipal waste stream. The treated medical waste residue is friable and can be compacted and compressed for weight volume reductions which may easily exceed 90 percent of that of the starting material. In the process, the high temperatures of the initial combustion chamber destroy any bacterial or viral pathogens which may be present on or within the waste. Where there is a significant ceramic or glass material present within the medical waste, the high temperatures will produce a molten glass product. If desired, additional glass formers can be added to the waste to create a vitrified waste product. The vitrified product may be useful as a way of encapsulating remnants of syringe needles or blades into a harmless solidified block. Such encapsulation would avoid the need for any further mechanical compressing, and may be a disposal method of choice for small volume generators of medical waste.

The present microwave treatment process is also compatible with the recovery of valuable metals as set forth in applicant's co-pending application entitled "METHODS FOR RECOVERING METALS FROM WASTE" and incorporated herein by reference having Ser. No. 09/199,696 filed Nov. 25, 1998. As a result, recyclable precious and non-precious metals can be removed from the waste stream.

The present invention has useful applications for small scale medical waste generators, such as individual physician's offices, veterinary practices, dentist offices, and research or clinical laboratories. As stated earlier, conventional microwave units are compatible with a simple embodiment of the present invention. Features common to certain microwave ovens may be readily adapted to provide an improved operating efficiency for the present invention. For instance, programming capabilities for microwave ovens can be preset so as to provide a gradual increase in microwave energy and treatment temperatures so as to avoid a large release of off-gases. By using a preset program which conservatively raises the temperature over a gradual period of time, an individual user need not worry with determining the relative amounts of volatile organic materials which may be present within the waste. It is also possible to provide a door locking mechanism responsive to the internal temperature of the susceptor and/or medical waste treatment container so as to prevent the opening of the microwave unit until an adequate cool-down period has elapsed. This feature protects the operator from potentially serious burns as well as preventing a sudden influx of air into a partially combusted heated waste sample. The sudden influx of air could result in an unwanted flashing or combustion of the treated medical waste.

While one or more preferred embodiments of the invention have been described above, it should be understood that any and all equivalent realizations of the present invention are included within the scope and spirit thereof. For example, the present invention may be embodied with a variety of different microwave units. It should be understood by those of ordinary skill in this art that the present invention is not limited to these embodiments, since modifications can be made. Further, such variations from the preferred embodiment would be expected in large scale applications capable of handling the large volume generators of a hospital. Therefore, it is contemplated that any and all such embodiments are included in the present invention as may fall within the literal or equivalent scope of the following appended claims.

What is claimed is:

1. An apparatus for disposing of medical waste comprising:
    a first combustion chamber in communication with a first source of microwaves;
    a second combustion chamber in communication with a second source of microwaves, said second combustion chamber having an input region in communication with a first end of a hollow conduit, a second end of said conduit in communication with said first combustion chamber, said second combustion chamber further comprising a susceptor defining a gas permeable matrix;
    an exhaust port in communication with an output region of said second combustion chamber, wherein said evolved combustion off-gases from the first combustion chamber pass through said conduit into an input region of said second combustion chamber whereby said susceptor matrix is maintained at an effective temperature for further treating said off-gases, said treated off-gases exiting through said exhaust port.

2. A process of treating medical waste comprising:
    providing a supply of medical waste material within a combustion chamber;
    passing a fluid stream through said combustion chamber;
    exposing said medical waste material to a combination of microwave energy and radiant energy, said radiant energy supplied by a susceptor in proximity to said medical waste;
    directing off-gases from said first combustion chamber to a second combustion chamber;
    radiating said off-gases in said second combustion chamber with microwave and radiant energy;
    retaining said off-gases within said second combustion chamber until an effective amount of said off-gases are destroyed, thereby providing treated off-gases;
    venting said treated off-gases.

3. The medical waste process according to claim 2, wherein said second combustion chamber is maintained at an operating temperature of at least about 1000° C.

4. The process according to claim 2 further comprising supplying a pressurized gas stream in communication with said first combustion chamber, said gas stream directing said off-gases and airborne particulates to said second combustion chamber.

5. The process according to claim 4 wherein said first combustion chamber is positioned below the second combustion chamber.

6. An apparatus for disposing of medical waste comprising:
    a first combustion chamber for heating medical waste to a temperature sufficient to combust organic materials within the waste;
    a second combustion chamber in communication with a source of microwaves, the second combustion chamber having an input region in communication with combustion gases generated from the organic materials within the first combustion chamber, the second combustion chamber further comprising a susceptor defining a gas permeable matrix;
    an exhaust port in communication with an output region of the second combustion chamber, wherein the combustion off-gases from the first combustion chamber enter into an input region of the second combustion chamber whereby the susceptor matrix is maintained at an effective temperature for further treating the off-gases, the treated off-gases exiting through the exhaust port.

7. The apparatus according to claim 6 wherein the susceptor matrix is housed within a tube, the tube in communication with the input region of the second combustion chamber.

8. The apparatus according to claim 7 wherein the susceptor matrix comprises SiC.

9. The apparatus according to claim 8 wherein the SiC is in the form of small particulates forming a bed within the tube.

10. The apparatus according to claim 7 wherein the susceptor matrix comprises a plurality of filters.

11. The apparatus according to claim 10 wherein the plurality of filters are comprised of SiC.

12. The apparatus according to claim 6 wherein the susceptor matrix achieves an operating temperature of about between 1,000° C. to 1,200° C.

13. A process of treating medical waste comprising:
    providing a supply of medical waste material within a combustion chamber;

passing a fluid stream through the combustion chamber;

exposing the medical waste material to elevated temperatures, thereby combusting organic materials within the medical waste;

directing off-gases from the first combustion chamber to a second combustion chamber;

exposing the off-gases in the second combustion chamber with a combination of microwave and radiant energy;

retaining said off-gases within the second combustion chamber until an effective amount of the off-gases are destroyed, thereby providing treated off-gases;

venting the treated off-gases.

14. The process according to claim 13 wherein the step of exposing the off-gases in the combustion chamber with the combination of microwave and radiant energy further comprises directing the off-gases through a matrix of a susceptor material maintained at a temperature of between about 1,000° C. to about 1,200° C.

15. The process according to claim 13 wherein the step of exposing the medical waste material to elevated temperatures further comprises exposing the medical waste material to a combination of microwave energy and radiant energy, the radiant energy being supplied by a susceptor in communication with the microwave energy.

* * * * *